US006843881B2

(12) United States Patent
Kim et al.

(10) Patent No.: US 6,843,881 B2
(45) Date of Patent: Jan. 18, 2005

(54) DETECTING CHEMILUMINESCENT RADIATION IN THE CLEANING OF A SUBSTRATE PROCESSING CHAMBER

(75) Inventors: Bok Hoen Kim, San Jose, CA (US); Nam Le, San Jose, CA (US); Martin Seamons, San Jose, CA (US); Ameeta Madhava, San Francisco, CA (US); Michael P. Nault, Woodland Park, CO (US); Thomas Nowak, Cupertino, CA (US); Tsutomu Tanaka, Santa Clara, CA (US); Moshe Sarfaty, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 75 days.

(21) Appl. No.: 10/115,526

(22) Filed: Apr. 2, 2002

(65) Prior Publication Data

US 2003/0185966 A1 Oct. 2, 2003

(51) Int. Cl.$^7$ ............................................. H01L 21/306
(52) U.S. Cl. ............................ 156/345.25; 156/345.24; 156/345.29; 156/345.35; 156/345.51; 134/56 R

(58) Field of Search ...................... 156/345.24, 345.25, 156/345.29, 345.35, 345.51, 345.36, 345.37, 345.41; 134/56 R, 1, 1.1, 1.2, 1.3, 18, 19, 22.1, 34, 37, 57 R, 105, 902; 216/59, 60, 63, 67, 69, 79; 438/905

(56) References Cited

U.S. PATENT DOCUMENTS

| | | | | | |
|---|---|---|---|---|---|
| 4,427,516 A | * | 1/1984 | Levinstein et al. | ..... | 204/192.38 |
| 4,687,544 A | * | 8/1987 | Bersin | ......................... | 438/709 |
| 4,689,112 A | * | 8/1987 | Bersin | ......................... | 438/709 |

* cited by examiner

Primary Examiner—M. Kornakov
(74) Attorney, Agent, or Firm—Janah & Associates

(57) ABSTRACT

In a substrate processing apparatus, a substrate processing chamber has a substrate support to support a substrate, a gas delivery system to provide an energized cleaning gas to the chamber to clean process residues formed on surfaces in the chamber during processing of the substrate, and an exhaust to exhaust the cleaning gas. A detector monitors a chemiluminescent radiation emitted from about a surface during cleaning of the process residues by the energized cleaning gas and generates a signal in relation to the monitored chemiluminescent radiation. A controller receives the signal and evaluates the signal to determine an endpoint of the cleaning process.

15 Claims, 6 Drawing Sheets

DETECTING CHEMILUMINESCENT RADIATION IN THE CLEANING OF A SUBSTRATE PROCESSING CHAMBER

BACKGROUND

The present invention relates to detection of chemiluminescent radiation in the cleaning of substrate processing chambers.

In substrate fabrication processes, semiconductor, dielectric, and conductor materials, such as for example, polysilicon, silicon dioxide, aluminum and or tungsten silicide, are formed on a substrate by chemical vapor deposition (CVD), physical vapor deposition (PVD), oxidation, nitridation, ion implantation, and may be subsequently processed by etching processes. For example, in a typical CVD process, a reactive gas is used to deposit material on the substrate, and in a PVD process, a target is sputtered to deposit material on the substrate. In oxidation and nitridation processes, an oxide or nitride material, such as silicon dioxide or silicon nitride, respectively, is formed on the substrate by exposing the substrate to a suitable gaseous environment. In ion implantation processes, ions are implanted into the substrate. In etching processes, a patterned etch resistant mask of photoresist or oxide hard mask is formed on the substrate by lithographic methods, and the exposed portions of the substrate are typically etched by an energized gas to form patterned gates, vias contact holes or interconnect lines.

In such processes, it is often desirable to use a process monitoring method to monitor and control processing of the substrate to predetermine process stages or process endpoints. For example, it may be desirable to stop etching when a layer of material is etched through or etched slightly beyond its thickness (a small depth into the underlying material). It may also be desirable to stop a deposition, oxidation or nitridation process when a predetermined thickness of material is obtained.

Process endpoint detection may also be used to determine an endpoint of a chamber or substrate cleaning process. When substrates have been processed in a process chamber, process residues may be formed on the chamber or substrate surfaces. The chamber performance and the substrate contamination levels may be improved by preventing or removing accumulation of the process residues on the chamber surfaces. The residues on the substrate may also need to be cleaned prior to subsequent process steps. It is desirable, therefore to have a monitoring system which can accurately determine a process endpoint, or the point at which the process residues are adequately cleaned from the chamber or substrate surfaces.

Typical process monitoring methods detect a radiation emanating from the chamber to monitor the process and determine a process endpoint. These methods include, for example, plasma emission analysis in which an emission spectrum of a plasma in the chamber is analyzed to determine a spectral change that arises from a change in the material being etched—which may occur upon etching through a material—as for example taught in U.S. Pat. No. 4,328,068 which is incorporated herein by reference. Another example, U.S. Pat. No. 5,362,256, which is also incorporated herein by reference, discloses a method of monitoring a process by monitoring a plasma emission intensity at a selected wavelength and correlating variations in the plasma emission intensity with a process endpoint. However, plasma emission analysis occurs as a gas phase reaction in the plasma which may require chemical species to migrate from the substrate or chamber surface to the plasma environment. As a result, there may be a time lag between the process performed on a surface in the chamber, such as the substrate or chamber surface, and the detectable gas phase plasma emission. Also, plasma emission analysis is dependent upon a plasma being generated in the chamber.

Thus, it is desirable to have a process monitoring method and apparatus capable of monitoring a process, for example, to detect an endpoint of the process, such as a chamber cleaning process within the chamber. It is further desirable to have a process monitoring system which does not require the process gas to be energized to obtain detectable radiation emissions.

SUMMARY

A substrate processing apparatus comprising:
 (a) a substrate processing chamber having surfaces therein, the chamber comprising:
   (i) a substrate support,
   (ii) a gas delivery system to provide an energized cleaning gas to the chamber to clean the surfaces in the chamber, and
   (iii) an exhaust to exhaust the cleaning gas;
 (b) a detector adapted to monitor a magnitude of a chemiluminescent radiation emitted from about a surface in the chamber during cleaning of the surfaces and generate a signal in relation to the monitored radiation; and
 (c) a controller adapted to receive the signal and determine an endpoint of the cleaning process from a change in magnitude of the signal.

A substrate processing chamber comprising:
 a support capable of supporting a substrate during processing of the substrate;
 a gas delivery system to provide an energized cleaning gas in the chamber to clean surfaces in the chamber;
 an exhaust to exhaust the cleaning gas from the chamber; and
 means for determining an endpoint of the cleaning process by monitoring a magnitude of a chemiluminescent radiation emitted from about a surface in the chamber during cleaning of the surface.

A substrate processing method comprising:
 (a) processing one or more substrates in a chamber, thereby forming process residues on surfaces in the chamber;
 (b) providing an energized cleaning gas into the chamber to clean the process residues on the surfaces in the chamber; and
 (c) monitoring a chemiluminescent radiation emitted from about a surface in the chamber during cleaning of the process residues to determine an endpoint of the cleaning process.

A substrate processing method comprising:
 (a) processing one or more substrates in a chamber, thereby forming process residues on surfaces in the chamber;
 (b) cleaning the process residues on the surfaces by providing an energized cleaning gas into the chamber; and
 (c) determining an endpoint of the cleaning process by monitoring a chemiluminescent radiation emitted from about a surface and a non-chemiluminescent radiation emitted from the energized cleaning gas.

A substrate processing apparatus comprising:
(a) a substrate processing chamber having surfaces therein, the chamber comprising:
  (i) a substrate support;
  (ii) gas delivery system to provide an energized cleaning gas to the chamber to clean the surfaces, and
  (iii) an exhaust to exhaust the cleaning gas;
(b) one or more detectors to generate signals in relation to
  (i) a chemiluminescent radiation emitted from about a surface in the chamber during cleaning of the surface, and
  (ii) a non-chemiluminescent radiation emitted from the energized cleaning gas during cleaning of the surfaces; and
(c) a controller to evaluate the signals to determine an endpoint of a cleaning process.

DRAWINGS

These and other features, aspects, and advantages of the present invention will become better understood with regard to the following description, appended claims, and accompanying drawings which illustrate exemplary versions of the invention, where:

DESCRIPTION

Figure 1:
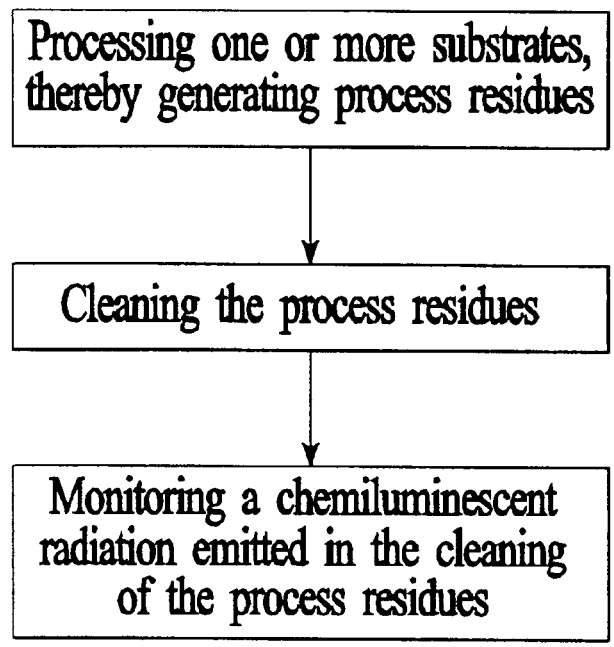
FIG. 1 is a flowchart of a process according to the present invention.

In the processing of a substrate 104a,b, it is often desirable to monitor the substrate process to obtain information about the process. For example, the substrate process may be monitored to control stages of the process or to determine an endpoint for the process, which is the time at which a stage, or the entire process, is substantially completed. In the present application, chemiluminescent radiation emanating from a processing chamber 106a,b is monitored. Chemiluminescent reactions release radiation in the form of photonic energy, such as for example, visible, ultraviolet or infra-red light. The intensity of this chemiluminescent radiation is monitored to determine a state of the process, such as a process endpoint. In a chemiluminescent reaction, photonic energy is released by an electronically excited species, or chemiluminescent species, such as a reaction intermediate or a reaction product, which is formed in a reaction. For example, when a process reaction yields a reaction product or intermediate species in an excited electronic state, relaxation of the species from the excited state to the electronic ground state emits photonic energy in the form of chemiluminescent radiation.

Monitoring the radiation emitted by the excited chemiluminescent species in the chemiluminescent reaction may be advantageous over plasma emission techniques which monitor the plasma emission radiation. For example, the chemiluminescent radiation may be monitored directly from near a surface region, for example from near a chamber surface 111a,b, wherein the chamber surface 111a,b is a surface 103a,b of a substrate 104a,b, a surface 107a,b of a chamber wall 602, or a surface of a chamber component. As this is typically the region of interest, the chemiluminescent radiation monitored from near a surface region is better representative of the progress of a chamber process than the radiation emitted by a gas phase reaction in a plasma. Also, monitoring chemiluminescent radiation is particularly beneficial when a process gas is energized in a remote chamber, as the energized gas typically does not emit radiation once it reaches the process chamber. Furthermore, this method does not require sustaining a plasma simply to monitor the process, as is done with plasma emission techniques.

In one exemplary method, chemiluminescent radiation from the reaction of a gas comprising a halogen with a silicon containing material, is monitored. When energized, the halogen containing gas forms radicals which react with the silicon containing material, for example, a silicon containing material present in process residues on a substrate 104a,b or on a surface 107a,b of a wall or component in the chamber 106a,b to yield chemiluminescent radiation. For example, reactions of fluorine or chlorine radicals with materials comprising one or more of silicon, polysilicon, silicon dioxide ($SiO_2$), silicon nitride ($Si_xN_yH_z$), silicon oxynitride (SiON) and silicon containing low k dielectrics may yield chemiluminescent radiation. Suitable halogen containing gases which form fluorine or chlorine radicals when energized may comprise one or more of $Cl_2$, $F_2$, $NF_3$, $CF_4$, $SF_6$, $C_2F_6$, $CCl_4$ and $C_2Cl_6$. It is believed that an example of a reaction involving a fluorine radical and a silicon containing material is:

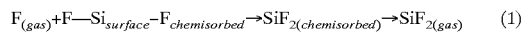
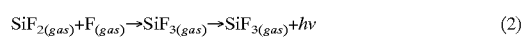

$$F_{(gas)} + F\text{---}Si_{surface} \text{---} F_{chemisorbed} \rightarrow SiF_{2(chemisorbed)} \rightarrow SiF_{2(gas)} \quad (1)$$

$$SiF_{2(gas)} + F_{(gas)} \rightarrow SiF_{3(gas)}^* \rightarrow SiF_{3(gas)} + h\nu \quad (2)$$

The fluorinated silicon species may be adsorbed onto a surface 111a,b in the chamber 106a,b, which may be a substrate surface 103a,b or a surface 107a,b of a wall or component in the chamber 106a,b. It is further believed that the fluorine radicals created by energizing a fluorine-containing gas, penetrate into the silicon containing layer and attack surface Si—Si or Si—N bonds, as in equation (1). The reaction may have two potential gaseous desorption products, the free radical $SiF_2$ and the stable end product $SiF_4$ (not shown). $SiF_2$ further reacts with F or $F_2$ (not shown) to form the excited state of $SiF_3^*$, which emits chemiluminescent radiation when it relaxes to a lower electronic state of $SiF_3$. While the chemiluminescent species produced in this example is an excited state of a product of the reaction, many other chemiluminescent reactions involve chemiluminescent atomic or molecular species formed as excited state intermediates in a reaction. These intermediate states may emit photons to return to their electronic ground states before completing the reaction to form the reaction products.

FIG. 1 illustrates a flow chart for a processing method in which chemiluminescent radiation is monitored in a cleaning process. The cleaning process at least partially removes process residue formed in, for example, a chemical vapor deposition, physical vapor deposition, or etching process. The removal of the process residues may be desirable, for example, to maintain processing uniformity for a batch of substrates, to extend the chamber lifetime, and to maintain effective functioning of the process chamber. In one version, the cleaning gas reacts with process residues deposited on a surface 111a,b in the chamber 106a,b to emit chemiluminescent radiation. For example, a deposition process in which a dielectric, for example one or more of silicon, polysilicon, silicon dioxide ($SiO_2$), silicon nitride ($Si_xN_yH_z$), silicon oxynitride (SiON) and silicon containing low k dielectrics, is deposited on a substrate 104a,b, may result in the formation of silicon containing process residue about a surface 111a,b in the chamber 106a,b.

In another version, chemiluminescent radiation is emitted by the reaction between the cleaning gas and a preselected chemiluminescent radiation emitting material lying under the process residues. For example, the chamber surface 111a,b may be pre-treated with material that reacts with the cleaning gas to emit chemiluminescent radiation before a substrate processing step that deposits process residue over the material. The chemiluminescent radiation emitted in the cleaning process may be monitored to determine the extent of cleaning of the process residues or the endpoint of the cleaning process, because chemiluminescent radiation is emitted when the process residues are at least partially cleaned and the energized cleaning gas reacts with the underlying chemiluminescent radiation emitting material In one version, a process may be performed to correlate the intensity of the chemiluminescent radiation emitted during a chamber process with the progress of the process. In a cleaning process, for example, the intensity of the chemiluminescent radiation emitted during or at the end of the optimal process, as well as the process parameters, such as the pressure in the chamber and the partial pressures of chemical species in the energized gas, may be detected, monitored or recorded. The chemiluminescent intensity obtained at the beginning, middle and end, of a test cleaning process, may be used to determine the endpoint of other processes. For example, when a cleaning gas reacts with process residues on a surface in the chamber, such as a surface 107a,b of the chamber wall 602 or on a substrate surface 103a,b, to emit chemiluminescent radiation, the intensity of the radiation may decrease from a first value to a second value which is lower than the first value. In one version, the intensity of the chemiluminescent radiation decreases towards zero or even to zero, when the process residue has been substantially cleaned. The change in intensity of the chemiluminescent radiation may be instantaneously detected, or monitored over time, to determine when the cleaning process is finished or when substantially all the process residues are removed.

In another version, for example, when a surface 111a,b in the chamber, such as the surface 107a,b of chamber wall 602 or components or substrate surface 103a,b is pre-treated with a chemiluminescent radiation emitting material which reacts with the cleaning gas to emit chemiluminescent radiation, the intensity of the chemiluminescent radiation may, instead, increase from a first lower value to a second higher value, at the cleaning endpoint. Initially, the chemiluminescent radiation is low or zero when process residues cover the chemiluminescent radiation emitting material, but after the process residues are cleaned, the chemiluminescent radiation emitting material is exposed to generate the chemiluminescent radiation signal, which may be detected. The material may comprise for example, one or more of silicon, polysilicon, silicon dioxide ($SiO_2$), silicon nitride ($Si_xN_yH_z$), silicon oxynitride (SiON) and silicon containing low k dielectrics. Such material emits chemiluminescent radiation when exposed to energized gas, such as halogen containing gas. In one version, the chamber 106a,b may be pre-treated with the chemiluminescent radiation material to coat a surface 111a,b of the chamber 106a,b, such as for example a surface 107a,b of the chamber wall 602. The coating may comprise a thickness of from about 200 Å to about 300 μm.

Alternatively, a process endpoint may be determined, for example, when the intensity of the chemiluminescent radiation has attained a substantially constant value for a period of time.

The intensity of the radiation monitored in a process should be monitored at a wavelength which is characteristic of the wavelength of radiation emitted during the process. Typically, the intensity of the chemiluminescent radiation is monitored using a detector sensitive to one or more wavelengths of the radiation generated in the chemiluminescent reaction. For example, the radiation wavelengths selected for monitoring may be close to the radiation wavelengths emitted in the chemiluminescent reaction. Such wavelengths are typically in the range of from about 140 nm to about 1500 nm, and may even be from about 200 nm to about 800 nm.

In another version, radiation having a plurality of wavelengths corresponding to chemiluminescent and non-chemiluminescent radiation emissions may be monitored separately during the process or even simultaneously. For example, wavelengths corresponding to non-chemiluminescent radiation, such as one or more of the radiation from a plasma emission spectrum or radiation reflected by the substrate 104a,b may be monitored in addition to wavelengths corresponding to the chemiluminescent radiation emitted during the chamber process. In one version, the non-chemiluminescent radiation may comprise the plasma emission spectrum of fluorine containing species. Such dual wavelength monitoring processes may involve monitoring radiation having wavelengths from about 200 nm to about 800 nm to detect a specific non-chemiluminescent radiation; as well as monitoring wavelengths in the chemiluminescent radiation range of, for example, from about 140 nm to about 1500 nm to detect the chemiluminescent radiation.

In one exemplary embodiment, the chemiluminescent radiation processing method may be used to monitor and determine an endpoint of a chamber process performed in a substrate processing apparatus, such as a Producer-type apparatus 100 comprising a twin PE-CVD dielectric deposition chamber from Applied Materials, Santa Clara Calif. The apparatus 100 comprises tandem processing chambers 106a,b which allows for the processing of multiple substrates 104a,b in a single processing environment, as for example, schematically illustrated in FIG. 2. The chambers 106a,b are defined by a chamber wall 602 and include two process zones 618, 620 in which individual substrates 104a,b are concurrently processed. The chamber wall 602 comprises a lid 604, sidewalls 612, bottom wall 616 and interior walls 614a,b which cooperate to define the two process zones 618, 620. Chamber liners 627a,b, which may be made of a ceramic material such as aluminum oxide or aluminum nitride, are disposed in each process zone 618, 620 to protect the chamber wall 602.

Figure 2:
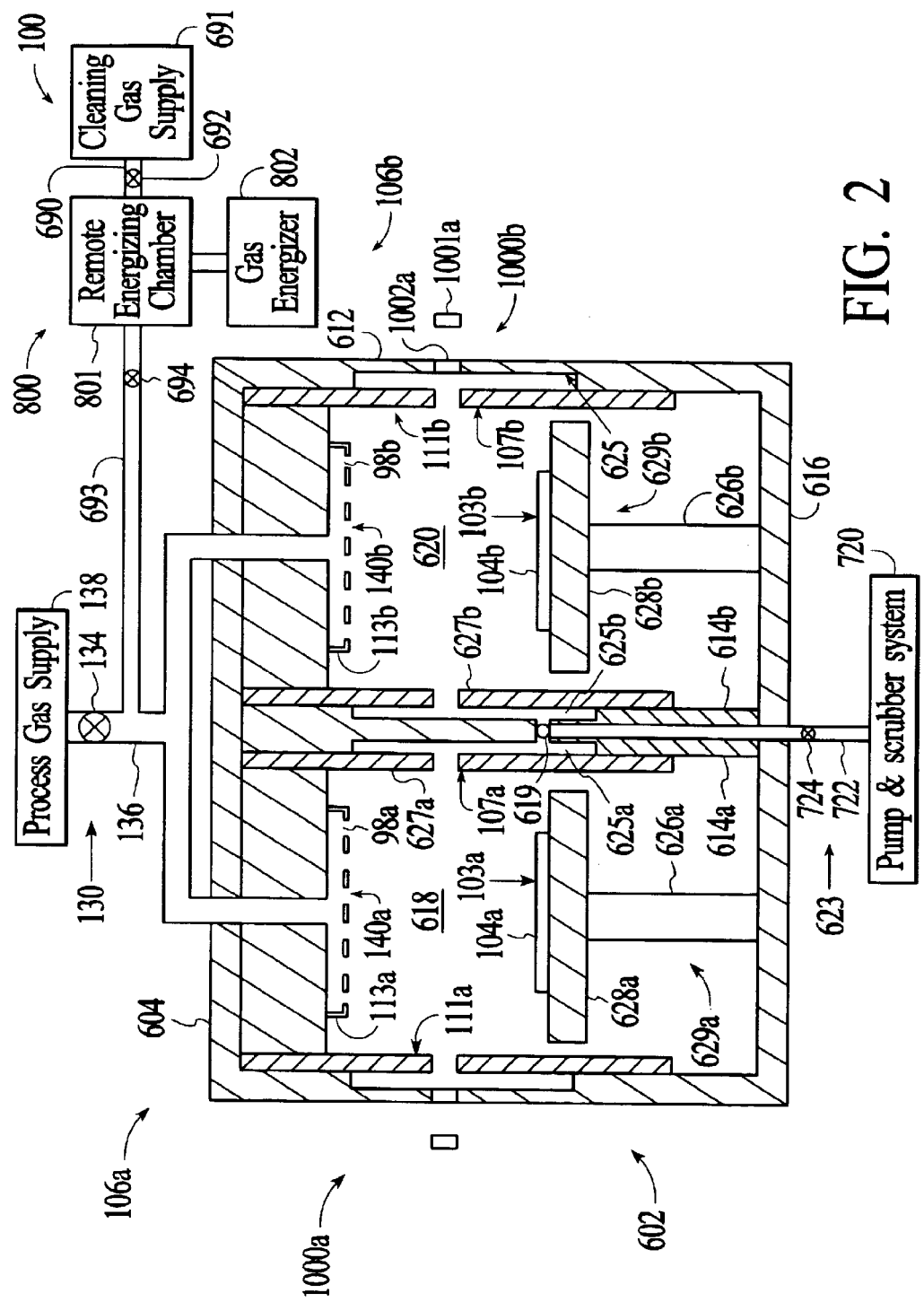
FIG. 2 is sectional schematic view of an exemplary process chamber according to the present invention, showing a chemiluminescent detector.

FIG. 2 further shows a substrate support 629a,b comprising a pedestal 628a,b in each process zone 618, 620, and further comprising a stem 626a,b which is connected to the underside of the pedestal 628a,b and extends through the bottom wall 616 of the chamber 106a,b where it is connected to a drive system (not shown). The stem 626a,b mechanically positions the pedestal 628a,b within the process zone 618, 620. Each pedestal 628a,b may include a heater (not shown) to heat a substrate 104a,b positioned thereon to a desired process temperature. The stem 626a,b moves upwardly and downwardly in the chamber 106a,b to move the pedestal 628a,b to position a substrate 104a,b thereon for processing or remove a substrate 104a,b therefrom.

A gas is introduced into the chamber 106a,b by a gas delivery system 130. In one version, the gas delivery system has gas flow valves 134 on a gas feed line 136 that transports gases from a gas supply 138 to the gas distributors 140a,b in each process zone 618, 620. The gas distributors 140a,b each comprise a gas distribution plate 113a,b having gas outlets 98a,b through which gas may exit the gas distributor 140a,b into the process zones 618, 620. The process gas introduced into the chamber 106a,b is exhausted by an exhaust system 623 that includes pumping channels 625a,b, an exhaust conduit 619, an exhaust line 722, a throttle valve 724, and a pump and scrubber system 720, which may include roughing and turbo-molecular pumps. The pumping channels 625a,b in each process zone 618, 620 circumferentially surround the process zones 618, 619 and receive the gas provided in each process zone 618, 620 for exhausting the gas. The pumping channels 625a,b of each process zone 618, 620 are connected to the shared pump and scrubber system 720 via the exhaust conduit 619 and the shared exhaust line 722. The exhaust conduit 619 is a port or channel that transports gas from the pumping channels 625a,b to the exhaust line 722 located at the back of the apparatus 100. The exhaust line 722 extends along the back of the apparatus 100 and connects the exhaust conduit 619 to the pump and scrubber system 720. The throttle valve 724 in the exhaust line 722 may be used to control the pressure of the gas in the chamber 106a,b.

The gas provided into the processing regions 618, 620 may be energized to, for example, deposit a dielectric material such as silicon dioxide on the substrates 104a,b. An energized gas may be formed from the gas provided in the chamber 106a,b by coupling electromagnetic energy into the processing regions 618, 620 of the chambers 106a,b. In one version, the gas may be energized by providing an RF bias potential to the gas distribution plate 113a,b to facilitate generation of an energized gas between the gas distribution plate 113a,b of the gas distributor and the pedestal 628a,b. An RF bias potential having one or more frequencies from 200 KHz to 60 MHz, and desirably about 13.56 MHz may be applied. The power level of the RF bias current may be from about 100 to about 3000 Watts.

The gas delivery system 130 may also comprise a remote plasma source 800 to deliver an energized cleaning gas to the chamber 106a,b. The energized cleaning gas may be provided into the chamber 106a,b to remove deposited material from the interior surfaces 111a,b of the chamber 106a,b after one or more substrate processing iterations. The remote plasma source 800 may comprise a cleaning gas supply 691, a remote chamber 801, a gas energizer 802 and gas transfer conduits 692, 694. Control valves 692, 694 control the flow of cleaning gas through the conduits 690, 693. The cleaning gas from the cleaning gas supply 691 may be transferred by the conduit 692 to the remote chamber 801 where the cleaning gas may be energized by a gas energizer 802. The gas energizer 802 couples electromagnetic energy to the cleaning gas to form reactive species. In one version, the gas energizer 802 couples microwave energy to the cleaning gas. The gas energizer 802 may comprise a 200 KHz to 2 GHz microwave generator, which may supply from about 500 Watts to about 8 Kilowatts to the remote chamber 801. Once activated, the cleaning gas is transferred by the gas transfer conduit 693 from the remote chamber 801 to the gas feed line 136. The gas feed line 136 delivers the energized cleaning gas to the gas distributors 140a,b in each process zone 618, 620.

An advantage of the remote plasma source 800 over in-situ plasma generators is that the gas energized by the remote plasma source 800 does not have to be sustained in the chamber 106a,b. This provides a more gentle method of cleaning the chamber 106a,b, as the gas is less energetic when it reaches the chamber 106a,b, and consequently, may be less erosive to the chamber components. Additionally, when the ions and electrons formed in the remote plasma source 800 have small lifetimes, the concentration of charged species which reach the chamber 106a,b may be negligible in comparison to in-situ cleaning processes. This reduces damaging ion bombardment of the chamber components. Thus, energizing the cleaning gas in the remote plasma source 800 increases the functioning lifetime of the chamber 106a,b and the chamber components.

In the processing of a substrate 104a,b in the chamber 106a,b, chemiluminescent radiation may be emitted. The emitted chemiluminescent radiation may be detected by a suitable chemiluminescent detector 1000a,b. The chemiluminescent detector 1000a,b should be positioned to detect chemiluminescent radiation emitted from the region of interest to monitor, for example, the intensity of the radiation. For example, when the chemiluminescent radiation is emitted in a surface reaction, the detector 1000a,b should be positioned to detect chemiluminescent radiation emitted from near a chamber surface 111a,b, such as for example, the substrate surface 103a,b or a surface 107a,b of a wall or component in the chamber 106a,b. Also, the chemiluminescent detector 1000a,b should have the sensitivity required to accurately detect the changes in the radiation intensity necessary to determine the endpoint. In one version, a suitable chemiluminescent detector 1000a,b may comprise a sensor 1001a,b, for example, a spectrometer, charge coupled device, or photodiode mounted to detect radiation passing through a window 1002a,b formed in a wall 602 of the chamber 106a,b that is permeable to chemiluminescent radiation of the desired wavelengths. In one version, the sensor 1001a,b comprises a photodiode with a bandwidth of 200 to 800 nm.

Figure 3:
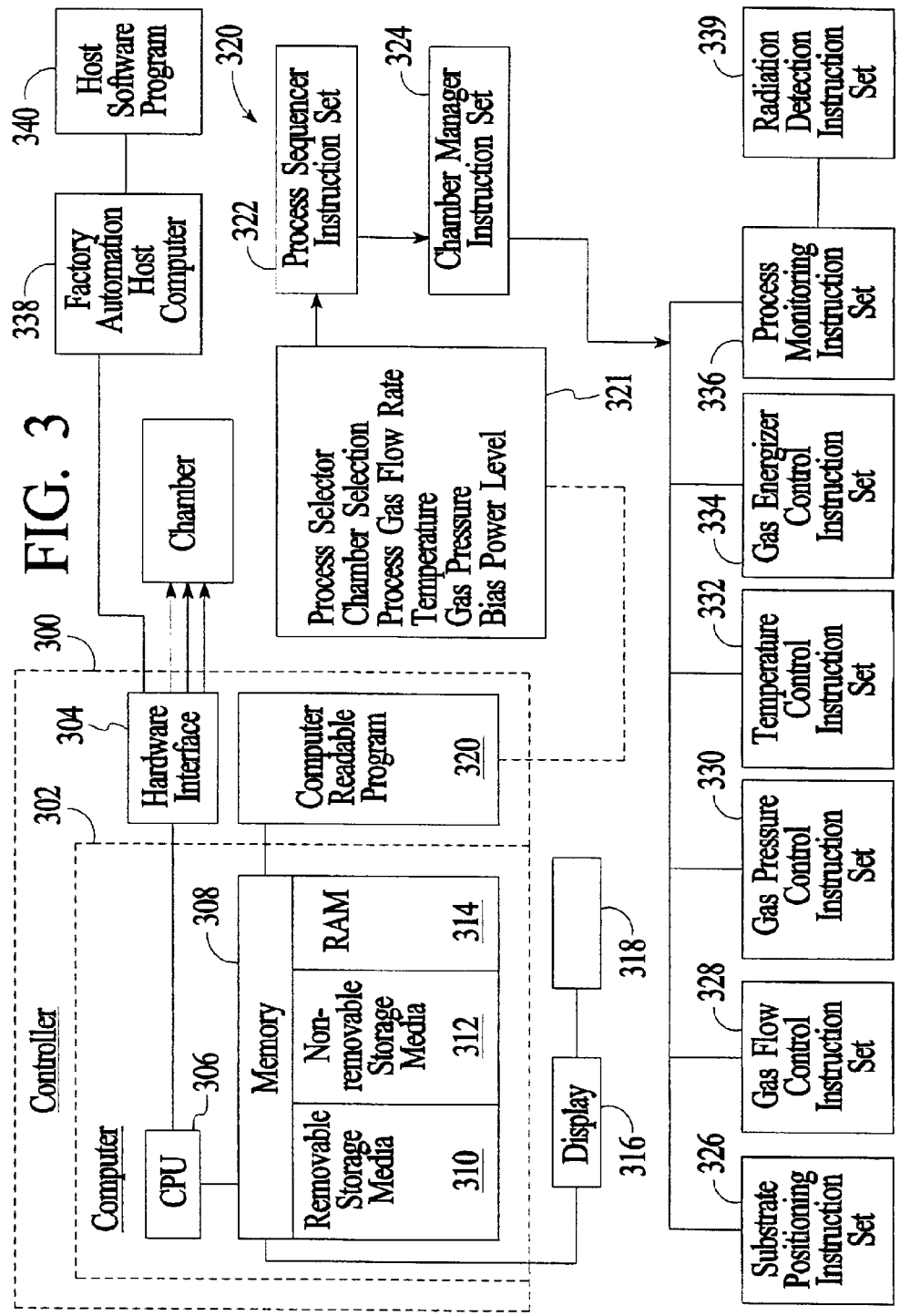
FIG. 3 is an illustrative block diagram of a controller and computer readable program.

The detector generates a signal in relation to the detected chemiluminescent radiation, which is passed to a controller 300 for evaluation. An illustrative block diagram of a controller 300 and associated computer program 320 is shown in FIG. 3. The controller 300 may comprise a plurality of interface cards including, for example, analog and digital input and output boards, interface boards, such as a hardware interface board 304, and motor controller boards. The controller 300 may further comprise a computer 302 which may comprise a central processor unit (CPU) 306, such as for example a 68040 microprocessor, commercially available from Synergy Microsystems, California, or a Pentium Processor commercially available from Intel Corporation, Santa Clara, Calif., that is coupled to a memory 308 and peripheral computer components, as shown in FIG. 3. Preferably, the memory 308 may include a removable storage media 310, such as for example a CD or floppy drive, a non-removable storage media 312, such as for example a hard drive, and random access memory 314. The interface between an operator and the controller 300 can be, for example, via a display 316 and a light pen 318. The light pen 318 detects light emitted by the monitor display 316 with a light sensor in the tip of the light pen 318. To select a particular screen or function, the operator touches a designated area of a screen on the monitor 316 and pushes the button on the light pen 318. Typically, the area touched changes color, or a new menu is displayed, confirming communication between the user and the controller 300.

The computer-readable program 320 may be stored in the memory 308, for example, on the non-removable storage media 312 or on the removable storage media 310. The computer readable program 320 generally comprises process control software comprising program code to operate the chamber 106a,b and its components, process monitoring software to monitor the processes being performed in the chamber 106a,b, safety systems software, and other control software, as for example, illustrated in FIG. 4. The computer-readable program 320 may be written in any conventional computer-readable programming language, such as for example, assembly language, $C^{++}$, Pascal, or Fortran. Suitable program code is entered into a single file, or multiple files, using a conventional text editor and stored or embodied in computer-usable medium of the memory 308. If the entered code text is in a high level language, the code is compiled, and the resultant compiler code is then linked with an object code of precompiled library routines. To execute the linked, compiled object code, the user invokes the object code, causing the CPU 306 to read and execute the code to perform the tasks identified in the program.

FIG. 3 also shows an illustrative block diagram of a hierarchical control structure of a specific embodiment of the computer readable program 320. Using the light pen interface 318, a user may enter instructions into the computer readable program 320 in response to menus or screens displayed on the CRT terminal. The computer readable program includes program code to control the substrate position, gas flow, gas pressure, temperature, RF power levels, and other parameters of a particular process, as well as code to monitor the chamber process. The process sets are predetermined groups of process parameters necessary to carry out specified processes. The process parameters are process conditions, including without limitations, gas composition, gas flow rates, temperature, pressure and plasma generator settings such as RF or microwave power levels.

The process sequencer instruction set 322 comprises program code to accept a chamber type and set of process parameters from the computer readable program 320 and to control its operation. The sequencer program 322 initiates execution of the process set by passing the particular process parameters to a chamber manager instruction set 324 that controls multiple processing tasks in the process chamber 106a,b. Typically, the chamber manager instruction set 324 includes a substrate positioning instruction set 326, a gas flow control instruction set 328, a gas pressure control instruction set 330, a gas energizer control instruction set 334, and a process monitoring instruction set 336. Typically, the substrate positioning instruction set 326 comprises program code for controlling chamber components that are used to load the substrate 104a,b onto the pedestal 628a,b and optionally, to lift the substrate 104a,b to a desired height in the chamber 106a,b. The gas flow control instruction set 328 comprises program code for controlling the flow rates of different constituents of the process gas. The gas flow control instruction set 328 controls the open/close position of the gas flow control valves, such as for example, gas flow control valves 134 to obtain the desired gas flow rate. The gas pressure control instruction set 330 comprises program code for controlling the pressure in the chamber 106a,b by regulating the opening size of the throttle valve 724 in the exhaust system 623 of the apparatus 100. The gas energizer control instruction set 334 comprises program code for energizing a gas in the chamber 106a,b or in the remote plasma source 800. For example, the gas energizer control subroutine 334 may comprise code for setting the RF bias voltage power level applied to process electrodes in the chamber 106a,b. As another example, the gas energizer control subroutine may comprise code to generate microwaves at pre-defined power levels in the remote plasma source 800. Optionally, a temperature control instruction set may be used to control the temperature of the chamber components such as the sidewalls 612 or the pedestal 628.

The process monitoring instruction set 334 comprises code for monitoring a process in the chamber 106a,b. In one version, the process monitoring instruction set 334 may comprise a radiation detection instruction set 339 to control the chemiluminescent detector 1000a,b. For example, the radiation detection instruction set 339 may comprise code to set detection parameters of chemiluminescent radiation or non-chemiluminescent radiation, such as ranges of wavelengths, or may comprise code to process a detected signal from the detection means. Additionally, the radiation instruction set 338 may comprise code which may determine the endpoint of a process according to a parameter set input by the operator. For example, the detector 1001a,b may deliver a signal related to the intensity of one or more of the detected chemiluminescent radiation or non-chemiluminescent radiation to the controller 300. The radiation detection instruction set 339 contained in the controller 300 may process the signal to obtain one or more of the chemiluminescent or non-chemiluminescent radiation signal as a function of time and wavelength. The endpoint of the chamber process may be determined by the radiation detection instruction set 339 once the radiation signal intensity has reached, for example, a pre-determined level for a certain amount of time. In one version of a cleaning process, the endpoint of the chamber process may be determined by the radiation detection instruction set 339 to be when the chemiluminescent radiation signal substantially decreases to a minimum value, and even, when the signal decreases to zero. A signal may be given by the radiation detection instruction set 339 to a factory automated host computer 338 to halt the chamber process once the process endpoint has been reached.

The data signals received by and/or evaluated by the controller 300 may be sent to the factory automation host computer 338. The factory automation host computer 318 may comprise a host software program 340 that evaluates data from several systems, platforms or chambers 106, and for batches of substrates 104a,b or over an extended period of time, to identify statistical process control parameters of (i) the processes conducted on the substrates 104a,b, (ii) a property that may vary in a statistical relationship across a single substrate 104a,b, or (iii) a property that may vary in a statistical relationship across a batch of substrates 104a,b. The host software program 340 may also use the data for ongoing in-situ process evaluations or for the control of other process parameters. A suitable host software program comprises a WORKSTREAM™ software program available from aforementioned Applied Materials. The factory automation host computer 338 may be further adapted to provide instruction signals to (i) remove particular substrates 104a,b from the processing sequence, for example, if a substrate property is inadequate or does not fall within a statistically determined range of values, or if a process parameter deviates from an acceptable range; (ii) end processing in a particular chamber 106a,b, or (iii) adjust process conditions upon a determination of an unsuitable property of the substrate 104a,b or process parameter. The factory automation host computer 338 may also provide the instruction signal at the beginning or end of processing of the substrate 104a,b in response to evaluation of the data by the host software program 340.

EXAMPLES

The following examples demonstrate the effectiveness of the present invention; however, the present invention may be used in other processes and for other uses as would be apparent to those of ordinary skill in the art and the invention should not be limited to the examples provided herein.

Example 1

In this example, process residues comprising different deposition film material that deposited on the wall 602 of the chamber 106a,b during deposition processes, were cleaned with a remotely energized cleaning gas comprising $NF_3$, to determine which deposition films may be cleaned and monitored for chemiluminescent emission radiation for endpoint detection. The chemiluminescent radiation from these cleaning processes were monitored through the chamber window 1002a,b by a chamber operator to detect chemiluminescent radiation wavelengths in the visible range, as illustrated in Table 1.

TABLE 1

| Deposition Film Type | Major Constituents | Chemiluminescent Radiation Color in Visible Spectrum |
|---|---|---|
| PE SiH4 and PE TEOS Oxide | SiO | None |
| PE Oxynitride and DARC ™ | SIONH | None |
| PE Nitride | SiNH | Bright Orange |
| Amorphous Silicon | SiH | Bright Orange |
| Single Crystal Silicon | Si | Soft White |

The experiment indicates that deposition film types without oxygen emit visible light which can be detected to determine the endpoint of a process. Although films comprising oxygen do not emit visible light upon reaction with $NF_3$, it may be possible to detect light having UV or IR wavelengths during these processes. It can be seen therefore, that detectable chemiluminescent radiation may be obtained through the reaction of a gas such as $NF_3$ with a material comprising silicon.

Example 2

Figure 4A:
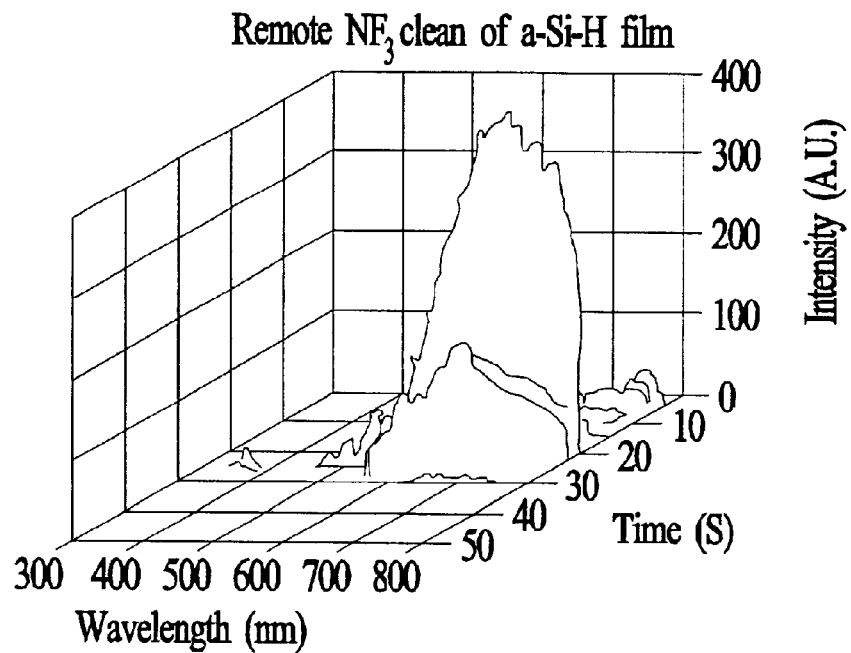
FIGS. 4a and 4b are graphs of the intensity of a chemiluminescent radiation signal for increasing time and wavelength.
Figure 4B:
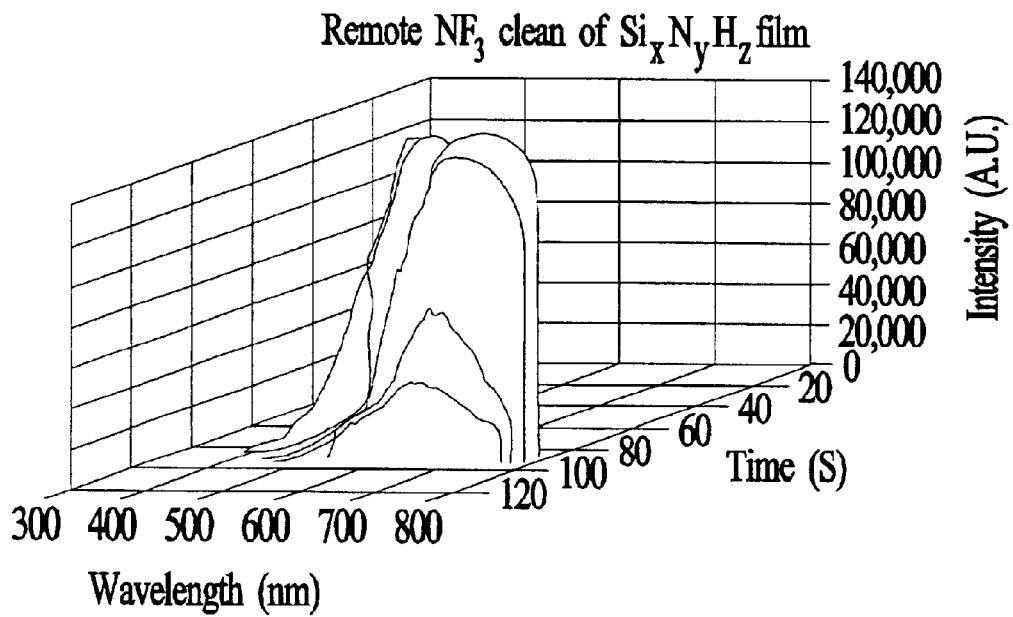

In this example, an amorphous silicon film and a silicon nitride film were cleaned by a remotely energized gas comprising $NF_3$ and spectra were obtained by monitoring the chemiluminescence emitted in the cleaning of the films with a photodiode having a bandwidth of 200 to 800 nm. FIG. 4a illustrates the spectrum for the cleaning of an amorphous silicon film. FIG. 4b illustrates the spectrum for the cleaning of a silicon nitride film. In both figures, the intensity of the radiation is graphed as a function of time for wavelengths from about 200 nm to about 800 nm. Both spectra are approximately centered around 750 nm. The chemiluminescent radiation spectra is time dependent, with the intensity of the radiation increasing towards the start of the process and decreasing towards the end of the process.

Figure 5A:
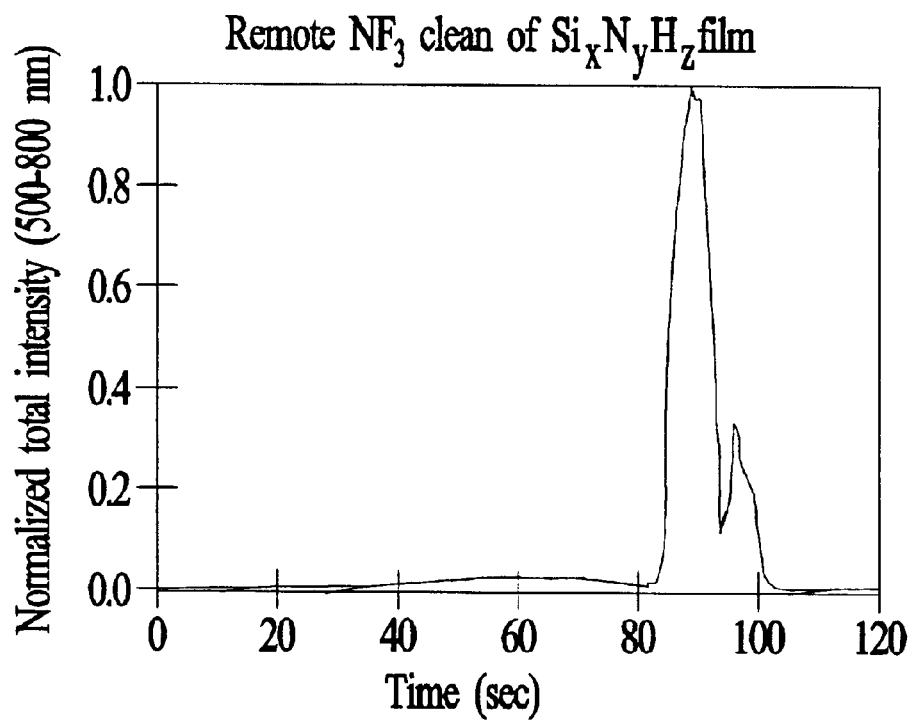
FIGS. 5a and 5b are graphs of the intensity of a chemiluminescent radiation signal for increasing time.
Figure 5B:
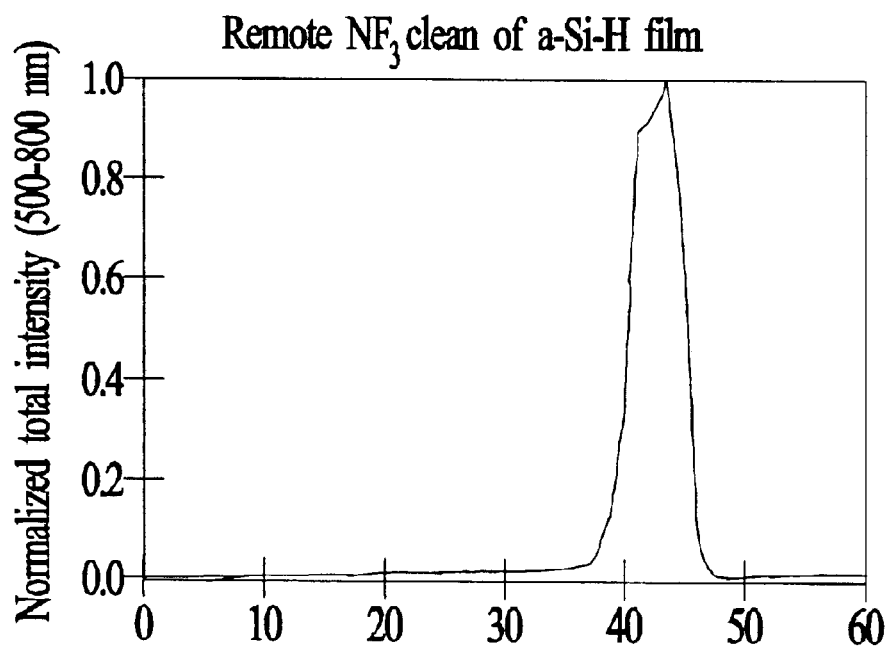

This time dependence is further shown in FIGS. 5a and 5b, which are graphs of the normalized chemiluminescent radiation intensity for increasing time for the cleaning of silicon nitride and amorphous silicon films, respectively. In both figures, the intensity of the radiation increases at the start of the chamber process and decrease toward zero at the end of the process. In the cleaning of the silicon nitride film, the intensity of the radiation increases to a maximum at about 85 seconds and decreases to zero after approximately 100 seconds. In the cleaning of the amorphous silicon film, the intensity of the radiation increases to a maximum at about 45 seconds and decreases to zero after approximately 45 seconds. These spectra show that the magnitude of the intensity of the chemiluminescent radiation emitted in the chamber process is sufficient to be detected and to distinguish between increases and decreases of the intensity of the chemiluminescent radiation during the process.

Example 3

Figure 6:
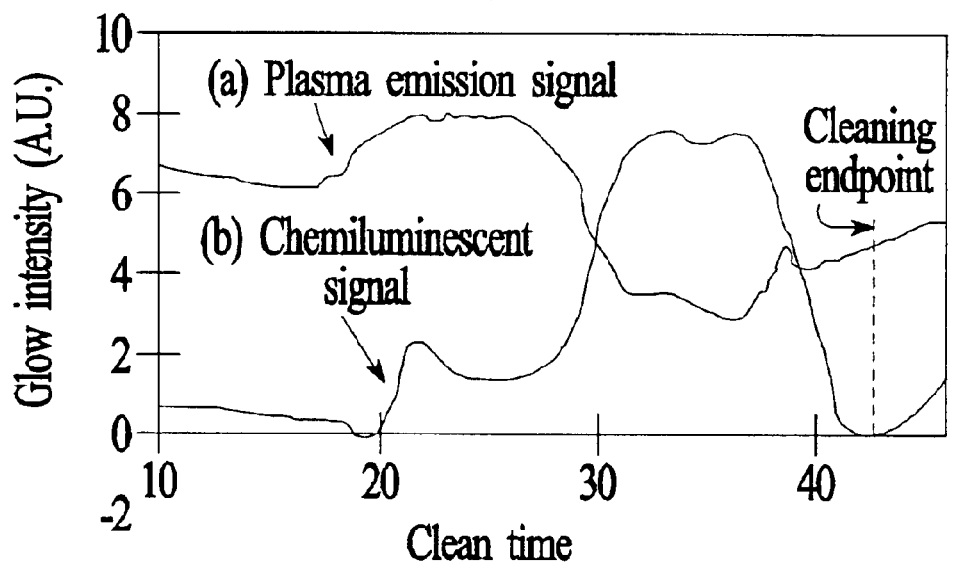
FIG. 6 is a graph of the glow intensity of (a) a chemiluminescent radiation signal, and (b) a plasma emission signal (686 nm after passing through a band pass filter) for increasing time.

In this example, the normalized intensities of chemiluminescent radiation emissions and effluent optical emissions for a cleaning process using a remotely energized cleaning gas comprising $NF_3$ are compared. In this example, chemiluminescent radiation was detected by a photodiode having a band width of 200 to 800 nm. Optical emissions were monitored by energizing the effluent from the process chamber in a downstream remote chamber and monitoring the emissions through a 686 nm sensitive band pass filter. The intensity was recorded for increasing time for the cleaning of a film comprising silicon, as shown in FIG. 6. The intensity of light emitted by the effluent at the endpoint of the process correlated well with the intensity of the chemiluminescent radiation. The relative minimum of the intensity of the chemiluminescent radiation at the endpoint of the process is advantageous over the effluent emission detection method and other plasma emission methods, because the minimum intensity point may be easier to detect than the slow rise in intensity provided by the effluent emission method. Additionally, as the endpoint occurs when all of the deposition film has been reacted with the cleaning gas, the minimum intensity is not dependent on the amount of cleaning gas used. In contrast, the intensity of the endpoint as determined by the effluent emission or other plasma emission is dependent on the amount of gas used, and therefore the intensity of the endpoint may need to be determined for new gas compositions or concentrations. Additionally, the magnitude of the change in intensities during and after the cleaning process is higher for the chemiluminescent radiation than for the plasma emission method, and this may allow the controller to more accurately determine the process endpoint. Thus, monitoring chemiluminescent provides an accurate and reliable method for determining the endpoint of a process.

Example 4

Figure 7:
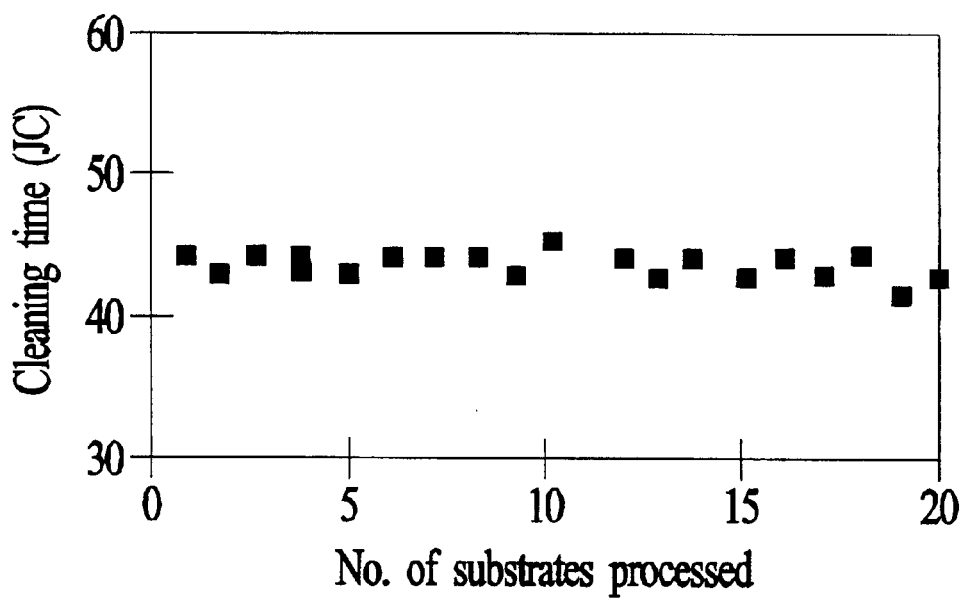
FIG. 7 is a graph of the cleaning time for cleaning processes monitored using a chemiluminescent radiation signal and for the processing of a number of substrates.

In example 4, the reliability of a chamber clean time as determined by chemiluminescent radiation monitoring, is demonstrated. In FIG. 7, the cleaning endpoint as determined by chemiluminescence radiation monitoring for the cleaning of a silicon containing film by a remotely energized cleaning gas comprising $NF_3$ is graphed versus the number of chamber cleans performed, each executed after a substrate deposition step. The chemiluminescent endpoint was determined by the point at which no visible light could be detected by a chamber operator. The chemiluminescent endpoint for the chamber cleaning can be seen to average about 55 seconds for 1 $\mu$m of depth, with a standard deviation of 2 seconds. Thus, the monitoring of chemiluminescent radiation provides a reliable method to determine the endpoint of chamber cleaning processes.

The present invention relates to a method and apparatus for determining the endpoint of a process in a process chamber by monitoring chemiluminescent radiation. The chemiluminescent radiation may be monitored by a detector 1000*a,b*, comprising for example a photodiode, positioned to receive chemiluminescent radiation emanating from process chamber 106*a,b*. In one version, the chemiluminescent radiation may be monitored for a cleaning process involving a remotely energized cleaning gas. The monitoring of chemiluminescent radiation provides an advantage over conventional plasma emission analysis techniques as a surface reaction within the chamber 106*a,b* may be reliably monitored with or without sustaining a plasma. Monitoring the chemiluminescent radiation from a chamber process provides for the reliable and efficient determination of the endpoint in a chamber process.

Although the present invention has been described in considerable detail with regard to the desired version thereof, other versions are possible. For example, the detector may comprise other detection systems equivalent in function to the illustrative structures herein. Also, other reactants other than those explicitly described may be used to provide the chemiluminescent reaction. Furthermore, the terms below, above, bottom, top, up, down, first and second and other relative or positional terms are shown with respect to the exemplary embodiments in the figures and are interchangeable. Therefore, the appended claims should not be limited to the description of the desired versions contained herein.

What is claimed is:

1. A substrate processing apparatus comprising:
   (a) a substrate processing chamber having surfaces comprising chamber wall surfaces and chamber component surfaces therein, the chamber comprising:
      (i) a substrate support,
      (ii) a gas delivery system to provide an energized cleaning gas to the chamber to clean the surfaces in the chamber, and
      (iii) an exhaust to exhaust the cleaning gas;
   (b) a detector adapted to monitor a magnitude of a chemiluminescent radiation emitted from a surface region near a chamber wall surface or chamber component surface during cleaning of the surfaces and generate a signal in relation to the monitored radiation; and
   (c) a controller comprising a computer-readable program adapted to receive the signal and determine an endpoint of the cleaning process from a change in magnitude of the signal.

2. An apparatus according to claim 1 wherein the detector comprises a photodiode sensor adapted to detect radiation having a wavelength of from about 140 nm to about 1500 nm.

3. An apparatus according to claim 1 wherein the controller is adapted to determine the cleaning endpoint when a magnitude of the signal changes from a first higher value to a second lower value.

4. An apparatus according to claim 1 wherein the chamber is a deposition chamber adapted to deposit a dielectric on a substrate.

5. An apparatus according to claim 1 wherein the gas delivery system comprises a remote gas energizer adapted to energize the cleaning gas with microwaves.

6. An apparatus according to claim 1 wherein the gas delivery system comprises a cleaning gas supply adapted to provide a cleaning gas comprising a halogen gas.

7. An apparatus according to claim 1 wherein at least one of the surfaces in the chamber is coated with a material capable of reacting with an energized cleaning gas to emit chemiluminescent radiation.

8. An apparatus according to claim 1 wherein the detector is adapted to monitor a magnitude of a chemiluminescent radiation emitted from about the chamber wall surface.

9. A substrate processing chamber having surfaces comprising chamber wall surfaces and chamber component surfaces therein, the chamber comprising:
   a support capable of supporting a substrate during processing of the substrate;
   a gas delivery system to provide an energized cleaning gas in the chamber to clean the surfaces in the chamber;
   an exhaust to exhaust the cleaning gas from the chamber; and
   means for determining an endpoint of the cleaning process by monitoring a magnitude of a chemiluminescent radiation emitted from a surface region near a chamber wall surface or chamber component surface during cleaning of the surfaces wherein the means comprises a computer-readable program.

10. A chamber according to claim 9 wherein the means comprises:
   (i) a detector adapted to monitor a magnitude of a chemiluminescent radiation emitted from a surface region near the chamber wall surface or chamber component surface during cleaning of the process residues by the energized cleaning gas and generate a signal in relation to the monitored radiation; and
   (ii) a controller adapted to receive the signal and determine an endpoint of the cleaning process from a change in magnitude of the signal.

11. An apparatus according to claim 9 wherein the means for determining the endpoint of the cleaning process is adapted to monitor a magnitude of a chemiluminescent radiation emitted from about the chamber wall surface.

12. A substrate processing apparatus comprising:
   (a) a substrate processing chamber having surfaces therein, the chamber comprising:
      (i) a substrate support;
      (ii) gas delivery system to provide and energized cleaning gas to the chamber to clean the surfaces, and
      (iii) an exhaust to exhaust the cleaning gas;
   (b) one or more detectors to generate signals in relation to
      (i) a chemiluminescent radiation emitted from about a surface in the chamber during cleaning of the surface, and
      (ii) a non-chemiluminescent radiation emitted from the energized cleaning gas during cleaning of the surfaces; and
   (c) a controller comprising a computer-readable program to evaluate the signals to determine an endpoint of a cleaning process.

13. An apparatus according to claim 12 wherein the detector comprises:
   a first sensor adapted to detect the chemiluminescent radiation; and
   a second sensor adapted to detect the non-chemiluminescent radiation.

14. An apparatus according to claim 13 wherein the second sensor is adapted to detect a non-chemiluminescent radiation comprising a plasma emission radiation emitted by energized fluorine radicals.

15. An apparatus according to claim 13 wherein the first sensor is adapted to detect radiation having a wavelength of from about 140 nm to about 1500 nm.

* * * * *